Figure 1:
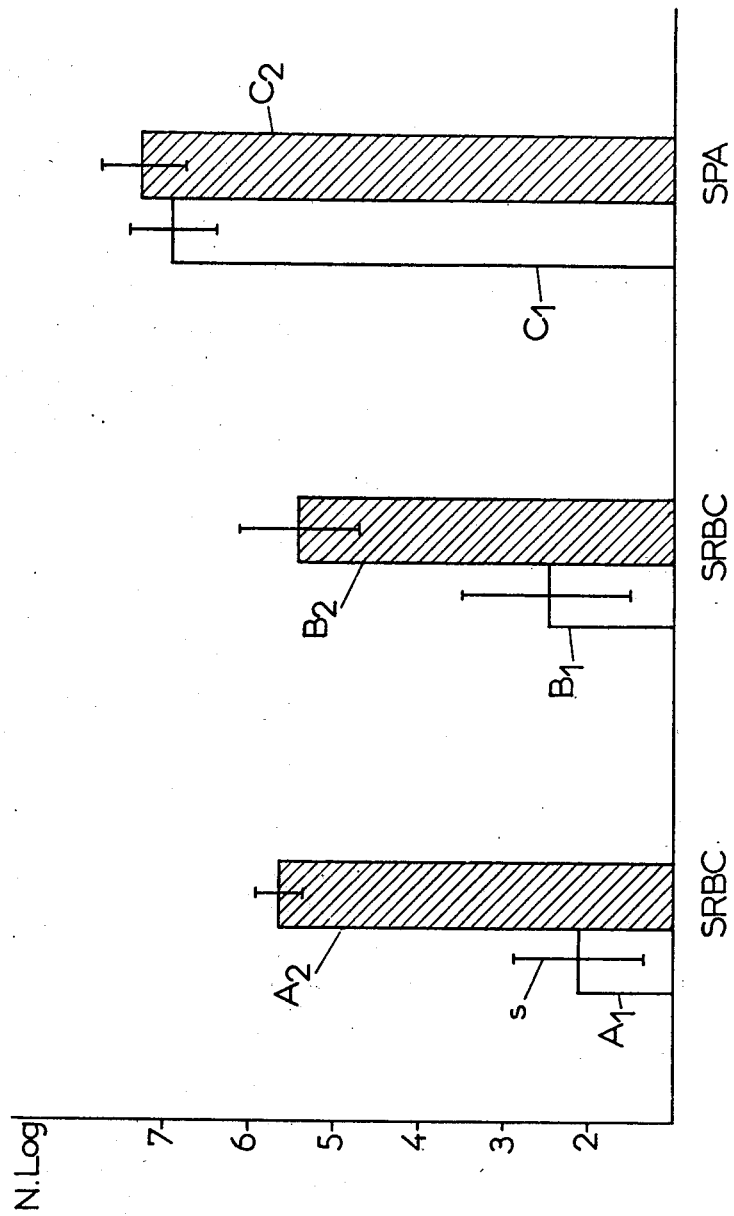

United States Patent [19]

Pierpaoli

[11] 4,310,535
[45] Jan. 12, 1982

[54] COMBINATION OF DRUGS AND A METHOD FOR THE SELECTIVE CONTROL OF THE IMMUNE REACTIONS EVOKED IN A HOST BY THE ADMINISTRATION OF ANTIGENS

[76] Inventor: Walter Pierpaoli, Bachtestrasse 23, Ebmatingen, Switzerland, CH-8123

[21] Appl. No.: 855,546

[22] Filed: Nov. 29, 1977

[30] Foreign Application Priority Data

Nov. 30, 1976 [GB] United Kingdom ............... 49826/76
Jun. 27, 1977 [GB] United Kingdom ............... 26817/77

[51] Int. Cl.$^3$ .................. A61K 31/40; A61K 31/415; A61K 31/445
[52] U.S. Cl. ............................... 424/273 R; 424/274; 424/267
[58] Field of Search ........................ 424/273, 274, 267

[56] References Cited

PUBLICATIONS

Chem. Abst., 74-61378d, (1971).
Chem. Abst., 76-81253d, (1972).
Chem. Abst., 66-52786t, 70-64912b.
Chem. Abst., 66-16927f, 26454g.
Chem. Abst., 85-116509g, (1976).
Chem. Abst., 9th Coll. Index, Chem. Subst. Palladium Alloy–Phosphono(thio), 27738–27739cs.

Primary Examiner—Stanley J. Friedman
Attorney, Agent, or Firm—Weiser, Stapler & Spivak

[57] ABSTRACT

The invention concerns a new composition or combination of drugs effective to selectively control the immune reactions which are evoked in a host by the administration of antigens.

It comprises active components capable of simultaneously blocking the α-adrenergic receptors of the cells for catecholamine, blocking the dopaminergic receptors of the cells and increasing the synthesis of serotonin. Preferred drug combinations according to the invention contain in association phentolamine, haloperidol, L-5-hydroxy-tryptophane and possibly dopamine.

9 Claims, 3 Drawing Figures

COMBINATION OF DRUGS AND A METHOD FOR THE SELECTIVE CONTROL OF THE IMMUNE REACTIONS EVOKED IN A HOST BY THE ADMINISTRATION OF ANTIGENS

The invention concerns a new composition or association of drugs effective to selectively control the immune reactions which are evoked in a host by the administration of antigens.

In the recent years increased interest has grown for the grafting of tissue or the transplantation, for instance of bone-marrow or organs from one host to another. Yet these techniques are considerably limited by the strong immune reactions which are evoked in the recipient and which cause the rapid rejection of the allogeneic grafts or transplants.

Considerable work and research have brought up a number of immunosuppresive agents, some of which are currently used despite the shortcomings and limitations which their administration entails (toxicity, side effects, etc.).

Such immunosuppressive agents include antibiotic and cytotoxic drugs, corticosteroids, antilymphocytic serum, etc. The manipulation of such agents and the control of their immunodepressive action are highly difficult, because of the length of the treatments and their general non-selective action which leaves the host without or at best with reduced defense with respect to antigens of all kinds.

An object of the invention is to overcome at least in part the above mentioned shortcomings and difficulties.

A general object of the invention is to provide a composition of drugs and a method for the specific control of the immune response of a host to selected exogenous antigens or group of antigens.

A more particular object of the invention is to provide a composition of drugs and method for selectively controlling, more particularly blocking the immune reactions of a host with respect to exogenous, such as allogeneic or even xenogeneic antigens or groups of antigens whenever this appears desirable.

In that respect the invention further aims at providing a treatment of shorter duration than heretofore and which is effective in blocking the immune reactions with distinctive selectivity in respect of determined antigens or groups of antigens administered to a host, while leaving the general immune capabilities of the host otherwise substantially unimpaired.

It will be appreciated that when reference is made hereafter to the selective blocking of the immune response to antigens, the latter word refers both to specific particular antigens or to specific groups of antigens.

The invention thus proposes a new drug composition, particularly a combination or association of active drug principles capable of inhibiting or delaying the neuroendocrine functions for the synthesis of gonadotropins or of the gonadotropins-releasing factors (LH-FSH-RF) in such manner as to block the initiation of the immune response and, thereby, to induce a complete specific unresponsiveness to antigens.

The drug composition according to the invention is characterized in that it contains active components such that said composition is capable, when administered to a host, of performing simultaneously the three functions defined hereafter, that is:

blocking the alpha-adrenergic receptors of the cells for catecholamines, blocking the dopaminergic receptors of the cells and increasing the synthesis of serotonin.

According to one preferred embodiment of the invention, said drug composition comprises at least three distinct components, each of which is capable of performing one of said three functions respectively.

A favorable combination according to the invention of such three drugs includes 2-[N-(m-hydroxyphenyl)-p-toluidine-methyl]-imidazolin, or a pharmaceutically acceptable salt thereof, particularly its methanesulfonate, also known under the generic name "Phentolamine" and abbreviated herein as PHE (of formula (I) in the table hereafter); 4-[4-(p-chlorophenyl)-4-hydroxy-piperidino]-4-fluorobutyrophenone-ethylamine, or a pharmaceutically acceptable salt thereof, particularly its hydrochloride, also known under the generic name "Haloperidol" and abbreviated herein as HAL (of formula (II) in the table hereafter) and 5-hydroxytryptamine (5-TP), also known under the generic name Serotonin, or preferably, its precursor L-5-hydroxy tryptophan (5-HTP) because 5-TP does not seem to be able to cross the blood-brain barrier (see formulae (III) and (IV)).

The invention derives from the finding that antigen challenge evokes prompt changes in the host hormonal status, involving primarily the levels of gonadotropins (i.e. luteotropic hormone (LH), and follicle stimulating hormone (FSH). More particularly it is suggested that binding of antigen to antigen-sensitive lymphocytes leads to the uncovering of receptors for hormones (LH, FSH and possibly ACTH and GH) on their membranes and/or synthesis and release of lymphokines (chemical messengers) to the hypothalamus-pituitary system. This provokes a decrease of circulating gonadotropins with consequent stimulation of releasing factors (LH-FSH-RF; CRF) due to a feed-back mechanism and/or direct action of lymphokines, thus also an increased production of the corresponding hormones, which the antigen-sensitive-lymphocytes apparently need for their differentiation.

This increased and rapid production of the hormone levels was particularly brought to evidence by the following immunization procedure in mice;

Groups of male C3H/HeJ inbred mice (three mice per group, 5 month-old) were inoculated intravenously (i.v.) with a suspension containing $5 \times 10^7$ lymph node lymphocytes from normal untreated or allo-immunized (injected four weeks earlier with spleen cells from C3H/HeJ mice) C57BL/6J mice. Control groups were inoculated with the same number of syngeneic cells (C3H/HeJ) or with the suspension medium (Gey's solution). Groups of mice were exsanguinated at 0.5, 1, 2, 3, 4, 5, 6, 7 and 8 hours after inoculation of the cells. The sera from each group were pooled separately, divided into aliquots and frozen until the radioimmunoassay of the protein hormones (LH, FSH, GH and prolactin) were performed. The levels of LH remained at normal values in the controls, (approximately 30–80 mg/ml). However, they were increased remarkably within 1 and 2 hours after injection of allogenic cells (over 250 mg/ml), and the increase was even more rapid (within 30 minutes to 1 hour) where lymph node cells from allo-immunized donors were utilized. Similar but less marked increases in levels of FSH were also observed.

It has been found that the combination of the three above drugs, when administered to a host a short time, such as one to two hours before the antigen, at dosages effective for performing the three above defined functions (that is: 1) blocking the alpha-adrenergic receptors: (2) blocking of the dopaminergic receptors: (3) increasing the synthesis of serotonin is able to induce unresponsiveness and antigenic tolerance, complete in humoral and partial in cell-mediated immune functions.

It is well known that phentolamine blocks the alpha-adrenergic receptors for catecholamines, haloperidol blocks the dopaminergic receptors, and the hydroxylated aminoacid 5-HTP, the immediate metabolic precursor of serotonin increases the synthesis of serotonin.

An hypothesis can be formulated according to which the first effects of the interaction of an antigen with the antigen-sensitive cells are the delivery of a message to the hypothalamic-pituitary centers. This results in changes in levels of gonadotropins in the blood. The alpha-blocker phentolamine blocks the alpha-adrenergic receptors at both the central (hypothalamus) and peripheral levels (cell membranes). Catecholamines, whose level is increased by haloperidol, a neuroleptic drug which blocks dopaminergic receptors, act on the free beta-adrenergic receptors, so provoking intracellular increase of cyclic AMP in the antigen-stimulated lymphocytes and inhibition of gonadropins and ACTH realease Finally serotonin, whose levels are increased by 5 HTP, will further complete the inhibition of the hormone production by the pituitary and, because it stimulates the serotoninergic receptors, particularly of the hypothalamus, thereby further inhibiting the ACTH releasing factor (CRF) and, accordingly, further hindering the production of the above said hormones (LH-FSH-RF) by the hypothalamus.

The above said combination of drugs does not, in all probability, act only on the central nervous system (hypothalamus) by affecting the secretion of hormones. A peripheral mechanism on other endocrine glands or on hormone receptors on membrane of unstimulated or antigen-activated bone marrow or thymus-derived lymphocytes is not excluded. Two components of the combination, e.g. haloperidol and phentolamine, might, by a competitive mechanism, bind to those receptors on the membrane of the antigen-sensitive lympocytes, which are the targets for the hormones involved in the initiation of the immune response. The catecholamines, whose level is increased by the neuroleptic drug haloperidol, and which are no longer effective on the alpha-adrenergic receptors, owing to the action of the alpha-blocker phentolamine, act on the beta-adrenergic receptors, provoking intracellular increase of cyclic AMP in the antigen-stimulated lymphocytes.

The hormone-dependent differentiation and cloning of the antigen sensitive lymphocytes is thus specifically and irreversibly blocked, leading to immune tolerance.

The humoral unresponsiveness and antigenic tolerance thus appears as correlated among other effects to the prevention of an increase in the serum of the treated host of the levels of the luteotropic hormone (LH) and follicle stimulating hormone (FSH) owing to the successive administrations first of the drug composition according to the invention and then of the antigens against which unresponsiveness is sought.

It is significant that the aboce three drugs are essentially ineffective individually. They must be administered together. As already indicated, the combination of these three drugs is capable of inducing complete unresponsiveness and antigenic tolerance in humoral immune responses. It does also induce at lease a remarkable reduction of cell-mediated immune functions. It has however been found that the decrease or even blockade of the latter immune functions is achieved also when using a fourth component in the association, i.e. (3,4-dihydroxyphenyl)-2-ethylamine, also called "dopamine," (of formula V), whereby release of the growth-hormone (GH) is presumably strongly reduced or even blocked. As a result the thymus cells are deprived of the GH supply which they normally require for ensuring cell-mediated immunity, more particularly for the differentiation of T-derived cells to immunocompetent cells.

These compositions are capable of producing a selective reduction and even blockade of the immune response to specific antigens, it being understood that the word "blockade" as used herein means the unresponsiveness of the treated host to the same antigen when the latter is again administered to it six months after the first sequential antigen-drug composition treatment.

The blockade of the humoral immune response is measurable by the substantial incapability of mice previously treated according to the protocol hereafter defined, of producing serum SRBC-antibodies, when injected again six months later with a same dose of sheep red blood cells (SRBC), said protocol comprising injecting intraperitoneally (i.p.) said mice with $4 \times 10^8$ SRBC and, starting from one to two hours before the latter i.p. injection, injecting sub-cutaneously once a day, during four days, a composition of L-5-hydroxytryptophan, haloperidol and phentolamine under proportions of 40, 12 and 12 mg per kg of body weight respectively/day (total dose: 160 mg 5 HTP, 48 mg PHE and 48 mg HAL per kg body weight).

In a similar manner the blockade of the cell-mediated immune response is measurable by the substantial incapability of mice previously treated according to the protocol hereafter defined and grafted with allogenic skin, of rejecting new allogenic skin transplants from the same histoincompatible donors 10 months after the end of the treatment according to said protocol, the latter comprising inoculating subcutaneously on the day of a first graft of said mice with the allogenic skin transplants (one or two hours before transplantation) with a composition containing L-5-hydroxytryptophan haloperidol, phentolamine and, but not necessarily dopamine, under proportions of 40, 12, 12 and 40 mg/kg of body weight respectively, and repeating said treatment every day with half of these doses further for 5-7 successive days.

Similar results might be achieved, at least partially, when substituting in the above combination any of its components by another which is capable of performing similar functions. For instance, any of the other alpha-adrenergic antagonists, such as the haloalkylamine series, i.e. dibenamine or phenoxybenzamine of respective formulae (VI) and (VII) can be substituted in the combination for phentolamine; any of the neuroleptics of the butyrophenone series, such as trifluperidol, methylperidol, pipamperone, flumisone, droperidol, of respective formulae (VIII) to (XII); can be substituted for haloperidol. The following compounds: iproniazid, fenelzina, pargylin, isocarboxazide, nialamide, iproclozide, tranylcypromine (MAOI, formulae XIII to XIX) or DOPA (3,4-dihydroxy-phenyl-α-alanine) might replace 5HTP and dopamine for increasing the levels of monoamines.

The process of the invention comprises administering the drugs to the host in the form of a composition containing the drug components in relative proportions and, as concerns each of them, in amounts effective to cause the selective blockade of the immune response of the host to the above said selected antigens administered later, the time interval between the administration of the drug combination and the administration of the antigens being adjusted such that the drug-combination is effective to block the increased production of the gonadotropins which would otherwise, in the absence of the combination of drugs, take place shortly after the moment of administration of said antigen to the host.

The time separating the first administration of the combination of drugs and the time of a first administration of the selected antigens is for instance of from one to twelve hours.

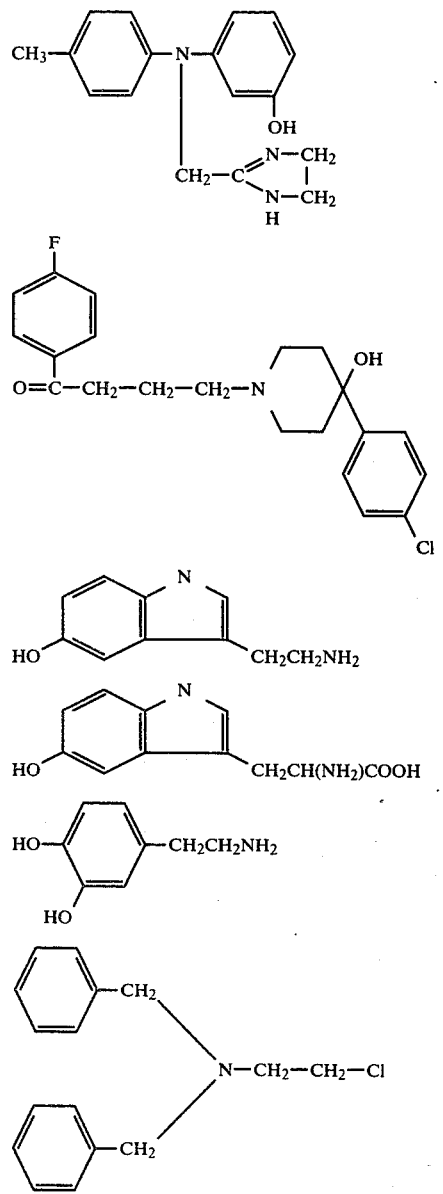

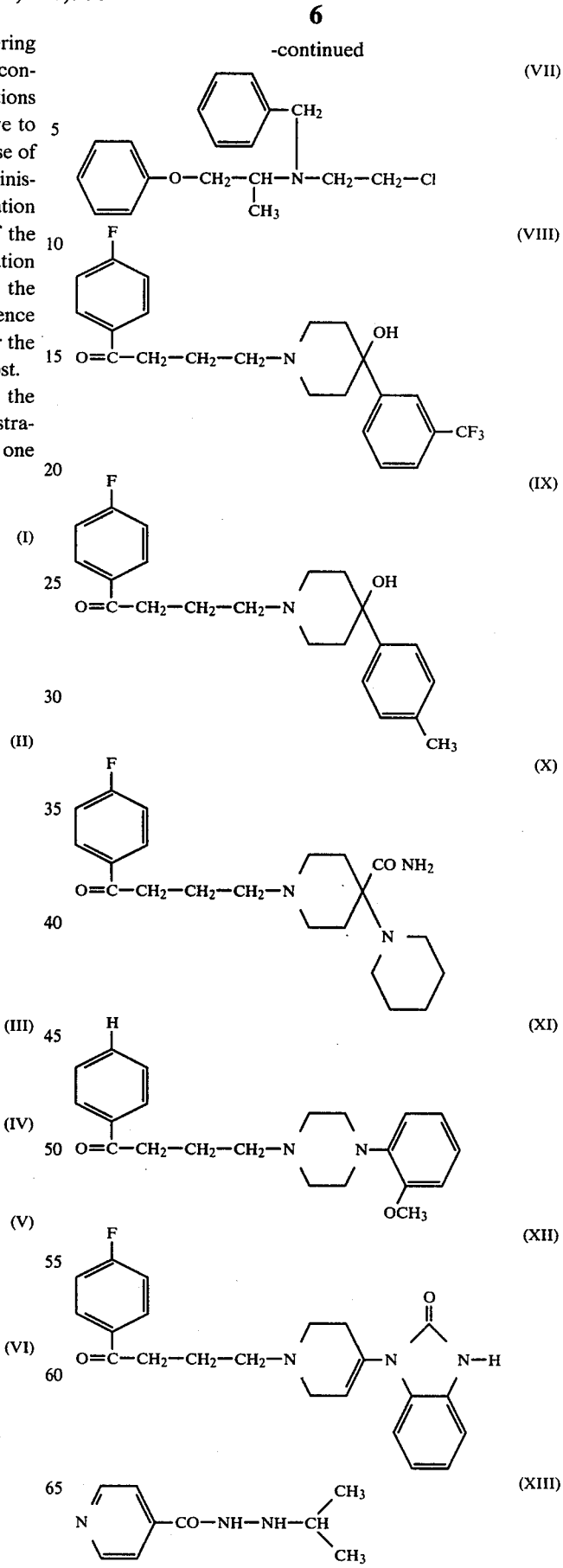

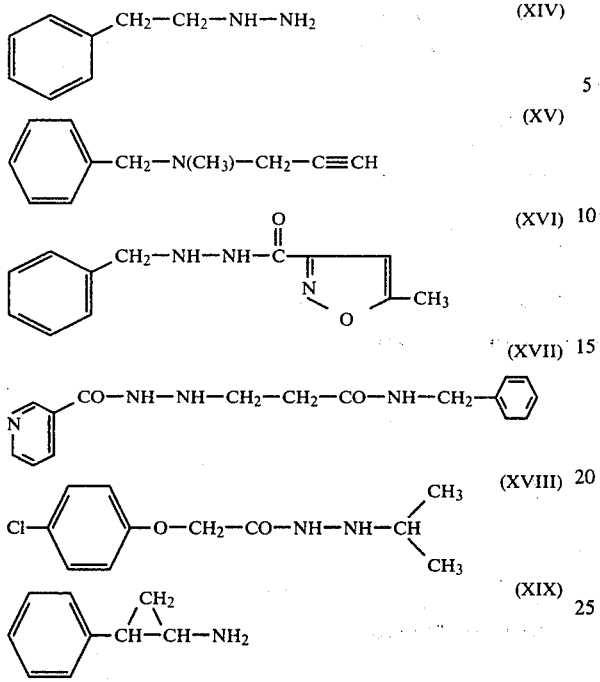

More particularly, the process according to the present invention comprises controlling the administration, more particularly adjusting the timing, the doses and the nature of the vehicles used such that the different drug components of the composition according to the invention be maintained present in the host during a total time sufficient, advantageously at least of about 48 hours, for permitting the selective blockade of the immune response to be obtained.

This may be obtained either by even but a single administration of an effective dosis of the drug composition according to the invention, when the latter is in a form such that its components are only released slowly in the body of the host.

This can be achieved particularly when resorting to an injectable suspension of the components of the drug composition in a medium in which they are all substantially insoluble.

For instance it has been found that the blockade of the immune response to a determined antigen, for instance SRBC, can be obtained by a single administration of the drug composition in the form of a suspension of its components in a saline solution.

Similar results are obtained when the drug composition is used in a solubilized form, such as in 0.5% solution of citric acid, said solution being however incorporated into Freunds's incomplete adjuvant.

The blockade of the immune response might however not be obtained in all instances with a monophased aqueous solution of an amount of the drug composition according to the invention which, when used in a medium of the type recalled hereabove, might prove sufficient for obtaining such blockade.

It has however been found that the same doses will prove fully effective even when all the components of the drug composition are solubilized in an appropriate solvent, provided that it be divided into a sufficient number of aliquots administered according to a sequence of injections at time intervals so spaced apart that all of the components of the composition to maintained present in the blood for the above defined sufficient total time, particularly with regard to 5-HTP and PHE which are known to be rapidly absorbed and to have half-lives which last but a few hours (it being understood that the first aliquot is to be administered, notably from one to two hours before the antigens).

In the latter instance one might also maintain the different components of the combination of drugs present in the blood of the host upon administering them by means of a perfusion. If needed the components of the combination may be used in the form of salts or derivatives thereof having improved solubility. For instance a mesylate of the 5-PHE may be substituted for the hydrochloride, to the extent where the first is more water-soluble than the second.

The invention will be further illustrated by the following non limiting examples, which disclose tests that have been run, some of which with reference to the drawings in which:

FIG. 1 is representative of haemagglutination titer reciprocals (normal logarithms with ±standard deviation shown by segments such as s on the axis of ordinates) measured on the sera originating from drug-treated mice (vertical white bands) and controls (vertical hatched bands) at determined times after injections of SRBC and of Shigella paradysenteria Antigens (SPA).

Figure 2:
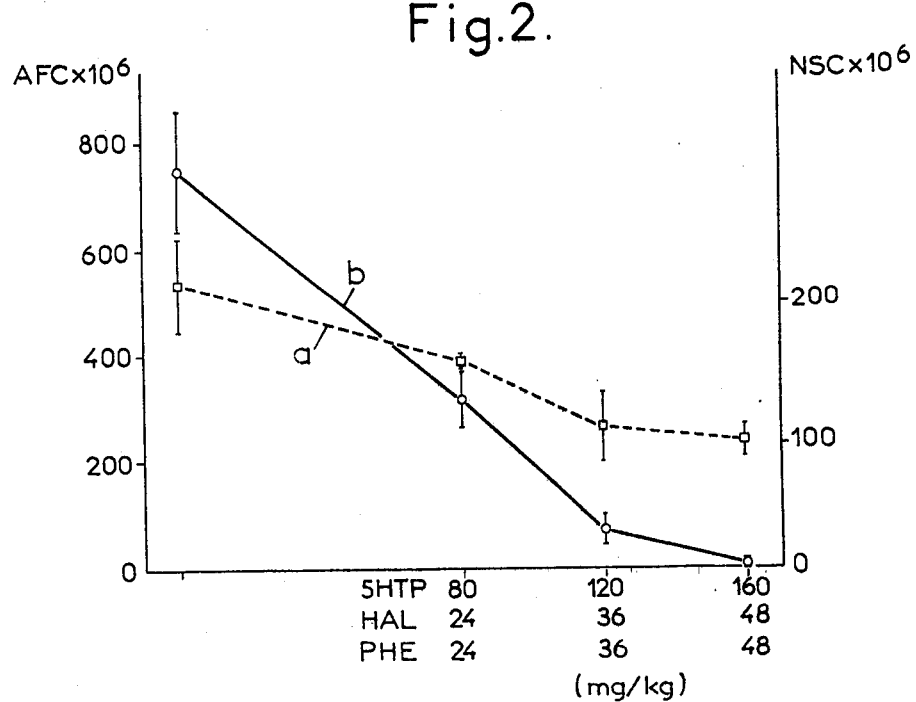
Figure 3:
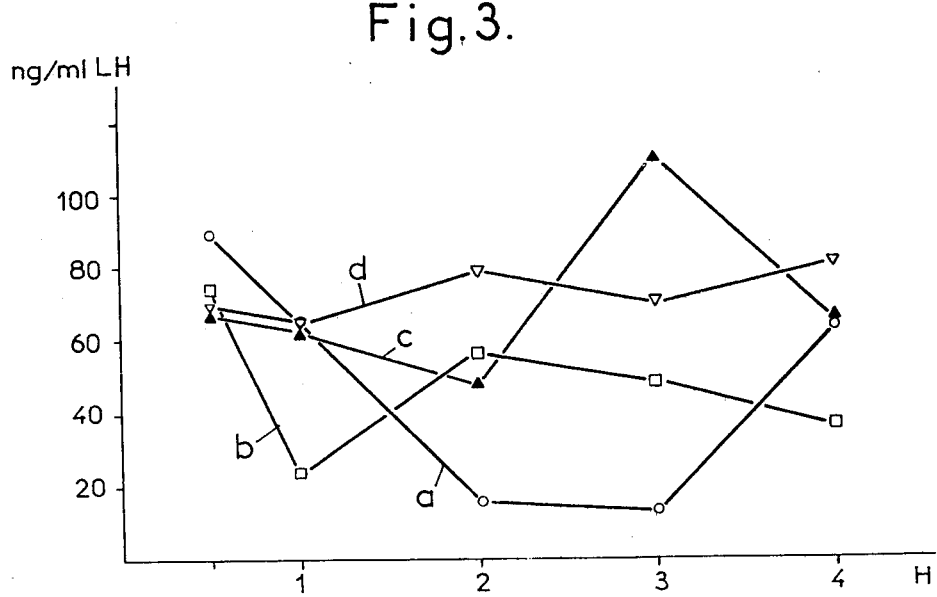

FIG. 2 comprises curves representative of the progressive inhibition in mice of antibody formation to SRBC obtained by a drug composition according to the invention dependent upon the doses used:

FIG. 3 comprises curves representative of the variation of the concentrations of the LH hormone in the serum of animals injected with sheep red blood cells (SRBC), on the one hand, and SRBC plus drugs on the other hand and further with the medium alone as a function of time.

The two following types of tests have been restored to in examples I and II hereafter.

The induction of a complete unresponsiveness and antigenic tolerance, or complete suppression of the humoral immune functions is brought to evidence by the test in which sheep red blood cells (SRBC) are injected into mice treated with a combination of phentolamine, haloperidol and 5-HTP. This produced a complete blockade of antibody production to SRBC.

The capability of a combination of drugs comprising the above said three components, plus dopamine, of interfering in cell-mediated (delayed hypersensitivity) immune reactions was determined by its ability to inhibit allogeneic skin graft rejection in adult mice and runt disease (graft versus host reactions) in newborn albino recipient mice when donors of spleen cells ($2 \times 10^7$ per newborn mouse i.p.) were untreated, drug-treated, and allo-immunized (with albino spleen cells from albino mice four weeks earlier) and drug treated C57BL/6J mice.

EXAMPLE 1

Immunological unresponsiveness to sheep red blood cells (SRBC) induced in mice by a combination of phentolamine, haloperidol and 5-HTP Adult (4–5 month-old) female C3H/HeJ mice were injected intraperitoneally (i.p.) with $4 \times 10^8$ SRBC. The number of direct plaque forming cells (PFC) was estimated 4 days after antigen injection. In some groups (memory response), $4 \times 10^8$ SRBC were reinjected at day 12 after the first inoculation and the number of direct PFC was measured 2 days later. One to two hours before the first antigen injection and then once a day for three consecutive days, a mixture of the three drugs was administered subcutaneously (s.c.) at the following doses: L-5-hydroxytryptophan, 40 mg/kg body weight; haloperidol, 12 mg/kg body weight; phentolamine, 12 mg/kg body weight. The drugs were dissolved in 0.5 percent citric acid and incorporated into Freund's incomplete adjuvant (FIA). In other experiments, the drugs were administered s.c. in a saline suspension (non-solubilized) as one unique cumulative dose corresponding to the whole dose of four days. The results appear in Table 1.

TABLE 1

Immunological unresponsiveness to sheep red blood cells (SRBC) in mice induced by a mixture of three drugs

| Treatment | PRIMARY RESPONSE | | |
|---|---|---|---|
| | N° of mice | Nucleated cells/spleen($\times 10^6$) | PFC/$10^6$ spleen cells |
| SRBC + DRUGS | 16 | 123 ± 45 | 5 ± 5 |
| SRBC | 18 | 208 ± 43 | 636 ± 165 |
| | MEMORY RESPONSE | | |
| | N° of mice | Nucleated cells/spleen($\times 10^6$) | PFC/$10^6$ spleen cells |
| SRBC + DRUGS | 16 | 231 ± 43 | 12 ± 12 |
| SRBC | 6 | 269 ± 32 | 520 ± 290 |

The table shows that complete inhibition and blockade of the primary and secondary (memory) response to SRBC (formation of direct, IgM-producing, plaque forming cells, PFC: Table 1).

This block could be prevented by pre-treatment or by simultaneous inoculation of LH, FSH and ACTH (adrenocorticotropic hormone, Table II), thus attesting to the identity of the hormones involved in the early immune phenomena.

This was brought up by the following test,

Hormones (LH 200 μg/day; FSH 200 μg/day; ACTH, 5 μg/day were injected i.p. in three aliquots on day 0 and in two aliquots on days 1, 2 and 3. The drugs (same as doses on Table 1) were given s.c. on day 0 and for the three successive days. The order of administration of the drugs, the antigens and the hormone were according to the sequences indicated in the left column of table 2. Direct plaque forming cells (PFC) were estimated 4 days after antigen inoculation.

TABLE 2

Protection from and prevention of drug-induced blockade of antibody response to SRBC in mice by hormones.

| Innoculation sequence | N° of mice | Nucleated cells/spleen ($\times 10^6$) | PFC/AO$^6$ spleen cells |
|---|---|---|---|
| SRBC | 10 | 270 ± 41 | 554 ± 95 |
| DRUGS-SRBC | 10 | 130 ± 37 | 7 ± 5 |
| SRBC-DRUGS | 4 | 115 ± 74 | 49 ± 34 |
| DRUGS-HORMONES-SRBC-HORMONES | 8 | 141 ± 25 | 69 ± 21 |
| HORMONE-SRBC-HORMONES-DRUGS | 7 | 211 ± 40 | 368 ± 112 |

Most interesting table 2 shows that prevention of or protection against the drug-induced blockade of antibody formation was achieved only when the hormones were given prior to drug-antigen treatment. This indicates that competitive drug-hormones mechanisms are operative on the antigen-sensitive cells for their differentiation to antibody-forming cells. It is noteworthy that hormones are inefficient in protecting against the action of the drugs when given after antigen-drugs or after drugs-antigen inoculation. It must be stressed that also a complete blockade of formation of indirect plaques (IgG-producing cells) was achieved by the same procedure.

EXAMPLE II

Delay of first set allogeneic skin graft rejection in mice induced by a combination of four drugs Outbred Swiss albino mice were grafted with full-thickness skin from inbred (C57BL/6J mice by the conventional technique. The protective corset was removed after 8–10 days. The graft was considered viable only as long as no signs of rejection (infiltration, oedema or ischemia) were present. Most of the drug-treated mice kept the graft with increasing signs of rejection as long as 45–50 days. Recipient mice were inoculated daily s.c. on day of grafting (one to two hours before transplantation) and for two successive days with 40 mg/kg body weight L-5 hydroxytryptophan; 12 mg/kg body weight haloperidol, 12 mg/kg body weight phentolamine and 40 mg/kg body weight dopamine. Half this dose was then injected for further 5–7 successive days.

TABLE 3

Delay of first set allogeneic skin graft rejection in mice, induced by a combination of four drugs.

| | N° of mice | % viable grafts:days after grafting | | | | | |
|---|---|---|---|---|---|---|---|
| | | 10 d. | 15 d. | 20 d. | 25 d. | 30 d. | 35 d. |
| NORMAL | 15 | 10 (66%) | 0 | — | — | — | |
| DRUGS-TREATED | 50 | 50 (100%) | 45 (90%) | 34 (68%) | 21 (42%) | 15 (30%) | 0 |

The table shows that an impressive prolongation of rejection time to allogeneic grafts was obtained in outbred albino mice transplanted with skin from inbred C57BL/6J mice. In this case dopamine in the drugs combination contributes to the blocking and decrease of the release of growth hormone (GH), which is known to be relevant for the differentiation of T-derived cells to immunocompetent cells, such cells being needed for a normal function of transplantation immunity. It must be considered that the criterion used for a complete "take" of the graft was the complete absence of any sign of ischemia and infiltration. Most of the grafts showing some signs of ischemia were otherwise kept for as long as 40 to 50 days, showing that the mechanisms of rejection are extremely weakened. The second-set rejection time to the same allogeneic graft in the same animals was the same, as indicating that no recovery of immune competence to the same antigens had occured.

III—Prevention of runt disease by drug-induced tolerance in allogeneic mice

Outbred newborn Swiss albino mice were injected i.p. on day of birth with $2 \times 10^7$ spleen cells from C57BL/6J donors which were untreated, or alloimmunized (with spleen cells from albino mice 4 weeks beforehand.). Groups of donors of each kind were also treated with the drug combination so as to render them "unresponsive". Dosage of drugs in the donor mice was as indicated on Table 4. No runting disease occured after four weeks of age.

TABLE 4

Prevention of runt disease in newborn albino mice by drug-induced tolerance in allogenic donor mice.

| Spleen cell donors: 57BL/6J mice | N° of injected newborn mice | % of surviving mice: age and days after cell injection | | | |
|---|---|---|---|---|---|
| | | 7 d. | 15 d. | 21 d. | 27 d. |
| Untreated | 31 | 93% (29) | 64% (20) | 32% (10) | 10% (3) |
| Alloimmunized | 10 | 100% (10) | 60% (6) | 30% (3) | 10% (1) |
| Alloimmunized and drugs treated | 38 | 100% (38) | 100% (38) | 94% (37) | 60% (23) |
| Drugs-treated | 23 | 91% (21) | 82% (19) | 56% (13) | 13% (3) |
| | 26 | 100% (26) | 100% (26) | 100% (26) | 100% (26) |

The table shows that a very pronounced suppression of the runting syndrome was obtained in newborn albino mice inoculated with spleen cells from C57BL/6J mice which had been previously made unresponsive to albino mice alloantigens by inoculation of albino mice spleen cells and drug treatment. Most of the animals of this group survived to this massive amount of incompatible cells ($2 \times 10^7$) which regularly killed most of the immuno-deficient newborn recipients belonging to the other groups. Moreover, the surviving mice showed milder symptoms of the GvH reaction-runt disease (exfoliative dermatitis, diarrhoea).

The following materials and methods were resorted to in the following examples III to X.

The animals used in these experiments were male or female inbred C3H/HeJ and BALB/c mice, C57BL/6J×CBA/J F1 hybrid mice and outbred Swiss albino mice. The age of the mice ranged from 2 to 8 months and the body weight from 20 to 40 grams. The animals were kept in groups of 4–5 per cage under conventional conditions, with free access to water and food. In order to minimize environmental stress, the mice selected for the experiments were separated and caged in groups a few days before the initiation of the experiments. Handling of the animals for the tests was also standardized (time of antigen inoculation and harvesting of cells for the tests).

The drugs used in the experiments mentioned below were: L-5-hydroxytryptophan (5HTP); phentolamine (PHE), haloperidol (HAL) and dopamine (DA). The drugs were administered subcutaneously (s.c.) either as saline suspension or as a solution in a 0.5% citric acid solution. The doses per Kg body weight and injection schedule varied according to the different experiments.

As regards the immunological tests for antibody production, sheep red blood cells (SRBC) in 20% saline suspensions and *Shigella Paradysenteria* Antigen (SPA) (prepared as disclosed hereafter) were the chosen antigens. Doses of $4 \times 10^8$ SRBC or 0.2 ml SPA were injected i.p. when required. The total number of nucleated spleen cells was counted in each individual mouse. Antibody production to SRBC was measured by the haemolytic plaque assay as number of antibody forming cells (AFC) per million spleen cells or by direct haemagglutination tests, 4 days after the injection of the antigen. Production of antibody to SPA was estimated by the direct agglutination test. When the number of direct and indirect (IgG-producing cells) plaques was measured, goat anti-mouse IgG antiserum at different dilutions (1:10, 1:100 and 1:500) was added to the plates after one hour incubation at 37° C.

The protein hormones LH and FSH were determined by radioimmunoassay (RIA). The kits for the determination were a gift from the National Institute of Arthritis, Metabolism and Digestive Diseases, Rat Pituitary Hormone Distribution Program, Bethesda, Md. U.S.A. (NIAMDD-Rat LH-3 and Rat FSH-I-3).

EXAMPLE III

The doses and modes of administration of the drug composition according to the invention:

The following example is to show the effectiveness of a combination of three drugs given once as a suspension or repeatedly as a solution, to block the primary immune response to SRBC.

Groups of four, five month-old C57BL/6×CBA F1 hybrid female mice were injected i.p. with $4 \times 10^8$ SRBC and the number of AFC was estimated four days later. The drug treatment was:

- A: drugs in saline suspension given once s.c. two hours before antigen;
- B: drugs solubilized in 0.5 percent citric acid, given once s.c. two hours before antigen;
- C: drugs in saline suspension given in four aliquots once a day for four days, starting 2 hours before antigen;
- D: drugs solubilized in citric acid given in four aliquots once a day for four days, starting two hours before antigen injection;
- E: SRBC only.

The total quantity of drugs given per mouse was: 5HTP, 160 mg, HAL 48 mg and PHE 48 mg per kg body weight.

The results are expressed both as the counts of the nucleated spleen cells $\times 10^6$ and as the number of antibody forming cells (AFC) per million spleen cells.

TABLE V

| Drug treatment | Nucleated spleen cells ($\times 10^6$) | AFC/$10^6$ spleen cells |
|---|---|---|
| A | 98 ± 10 | 2 ± 2 |
| B | 160 ± 19 | 323 ± 192 |
| C | 102 ± 32 | 9 ± 9 |
| D | 86 ± 21 | 4 ± 2 |
| E | 182 ± 17 | 828 ± 98 |

As is apparent from table V, the maintainance of a certain concentration of the drugs at the moment of antigen injection seems to be necessary for achieving the blockade of antibody production. The drugs completely solubilized and given in one single injection produced a moderate inhibition of antibody production while the same dose given as a saline suspension induced a complete blockade. However, the same amount of solubilized drugs induced a complete blockade when given in four aliquots within four days.

EXAMPLE IV

The maintainance of immune unresponsiveness or lack of memory response to SRBC in mice whose primary response to SRBC has been blocked by a combination of three drugs.

Groups of ten, 4 month-old female C57BL/6×CBA F1 hybrid mice were injected i.p. with $4 \times 10^8$ SRBC. The drugs were administered i.p. in saline suspension once a day for four successive days, at the following dosage, starting two hours before antigen injection: 40 mg of 5-HTP; 12 mg of PHE and 12 mg of HAL per kg of body weight.

Twelve days after the first antigen injection, the mice were injected again with the same amount of SRBC, and the number of direct (IgM-production) and indirect (IgG-producing) AFC was evaluated two days later.

TABLE VI

| Drug treatment | Nucleated spleen cells ($\times 10^6$) | IgM and IgG forming cells/$10^6$ spleen cells |
|---|---|---|
| Drugs + SRBC | 200 ± 25 | 15 ± 9 |
| SRBC | 250 ± 32 | 148 ± 86 |

As shown by table VI the blockade of the primary response to SRBC appeared to be persistent. As a matter of fact, the appearance of both IGM- and IgG-producing cells is completely abolished when the "blocked" mice are injected again with the same antigen.

EXAMPLE V

The specificity of the immune unresponsiveness for the antigen which has been administered in conjunction with the drug composition according to the invention:

This specificity was established by resorting to the following test.

One group of ten, three month-old SWR female mice was injected s.c. with a saline suspension of the three drugs combination two hours (40 mg 5HTP, 12 mg PHE and 12 mg HAL per kg. body weight) and 15 minutes (80 mg 5HTP, 24 mg PHE and 24 mg HAL per kg. body weight) before injection of the antigen (0.1 ml of 20% SRBC in saline suspension i.p.). The drugs were injected again at 20, 40 and 50 hours after injection of the antigen (40 mg 5HTP, 12 mg PHE and 12 mg HAL per kg body weight each time). One group of 6 mice was used as control and injected only with SRBC. The mice were bled 10 days after antigen injection and serum agglutinins were measured by direct agglutination test.

The heights of bands A1 (drug-treated animals) and A2 (for the controls) are respectively representative of the results then obtained. They bring to evidence the substantial blockade observed of the primary immune response as compared to that of the controls.

The same mice were then injected again with the same dosis of SRBC 67 days after the first antigen injection and the serum agglutinin titers were again determined three days later.

The heights of bands B1 and B2 of FIG. 1, here again, are representative of the results obtained. The difference in height of bands B1 and B2 shows thus the persistence of the unresponsiveness in the "blocked mice" subsequent to the SRBC second injection.

10 days after the second injection of SRBC, the same mice were injected intraperitoneally with 0.2 ml of the SPA antigen which had been prepared as described by HARAN GHERA, N. and PELED, A. in an article titled "The Mechanism of Radiation action in leukaemogenesis. Isolation of a leukaemogenic filtrable agent from tissues of irradiated and normal C57BL mice". Br. J. Cancer (1967) 21,730.

Production of antibody to SPA was estimated by measuring the agglutinin titer in accordance with the direct agglutination test as referred to in the above HARAN GHERA and PELED publication on serum taken up from said mice 7 days later.

The heights of the bands C1 and C2 are representative of the primary to SPA which were obtained in the drug-treated animals and controls respectively. These primary responses were substantially the same both in the drug-treated animals and controls.

This experiment thus demonstrates that the same mice, which were unresponsive to SRBC when injected with this antigen a second time 67 days after the first antigen and drug administration, were able to respond to *Shigella paradysenterie* Antigen (SPA) as efficiently as mice primed with that antigen. Therefore the long-lasting unresponsiveness induced to SBRC did not impair at all the ability of the same mice to respond to a second antigen.

EXAMPLE VI

The correlation between the concentration of the drug components of the composition according to the invention and the extent of immune inhibition.

Groups of five, four month-old male BALB/c mice were injected i.p. with $4 \times 10^8$ SRBC and the number of AFC was estimated four days later. The mixture of drugs was administered s.c. in one single injection as a saline suspension at the doses indicated on the axes of abscissae of FIG. 1, two hours before antigen injection.

The curves of FIG. 2 are representative of the variation of the rate of inhibition of antibody formation to SRBC expressed as the variation (curve a) of the number of nucleated spleen cells $\times 10^6$ (NSC $\times 10^6$ on the right hand side axis of ordinates) and the variation (curve b) of the number of antibody forming cells per $10^6$ spleen cells (AFC/$10^6$ on the left hand side ordinates) respectively dependent upon the respective doses of the active components of the composition according to the invention indicated in mg/kg of body weight (mg/kg on the axis of abscissae).

FIG. 2 thus shows that a correlation exists between the concentration of the components in the mixture and the extent of immune inhibition. It shows in particular that the blockade is complete in the treated mice for dosages as from 160 mg of 5-HTP, 48 mg of HAL and 48 mg of PHE per kg of body weight.

Similar tests may of course be run in other animal species to determine experimentally in each case which should be the respective dosages of the components of the drug composition according to the invention to be administered in conjunction with determined antigens, for the sake of causing a specific blockade of the immune responses against said determined antigens in these other animal species.

Although in no way limitative of the scope of the invention, it may be stated for mere indicative purposes that the proportions of the three or four components of the drug composition according to the invention (depending upon its containing dopamine or not) range advantageously from about 20 to about 150 parts of 5-HTP,
from about 5 to 15 parts of PHE,
from about 5 to 15 parts of HAL,
from about 10 to 50 parts of dopamine
(parts in weight).

EXAMPLE VII

Increase of LH level in blood of mice afer injection of SRBC. Its suppression by the drug composition according to the invention.

Groups of four-month old male C57BL/6×CBA/J Fl hybrid mice were injected in four different tests with (a) one single dose of a combination of three drugs s.c. (5HTP, 160 mg/kg, HAL, 48 mg/kg and PHE, 48 mg/kg body weight) suspended in saline; the same groups were injected i.p. with $4\times10^8$ SRBC one hour after injection of the drug;

(b) the combination of drugs;

(c) only SRBC and (d) the suspension medium (Gey's solution).

Groups of four mice each time were exsanguinated at 0.5, 1, 2, 3 and 4 hours after the inoculation of the SRBC. Sera from each time and group were pooled and frozen until determination of LH.

FIG. 3 shows curves a, b, c, which are respectively representative of the variations of the levels of LH in blood (in nanograms of LH per ml or ng/ml LH on the axis of ordinates) which were obtained in mice which underwent the four above mentioned a, b, c, d, respectively, dependent upon the time in hours (H on the axis of abscissae) after inoculation of the SRBC.

More particularly, FIG. 3 shows that i.p. injection of $4\times10^8$ SRBC into mice induced a sharp elevation of LH level at three hours after antigen injection. Injection of the drug composition only induced a sharp decrease of LH at one hour after drug inoculation. Finally, inoculation of SRBC in drug-treated mice induced a deep and protracted depression of LH in blood. The level of LH returned to normal values at four hours after the SRBC injection. The difference in level of LH between the antigen-treated and the drug- and antigen-treated mice was as high as 100 ng/ml.

EXAMPLE VIII

Inability of luteotropic hormone (LH) thyrotropic hormone (TSH) and growth hormone (GH) given singly or in combination to prevent the drug-induced inhibition of the immune response to SRBC:

Groups of four, 4 month-old C3H/He male mice were injected i.p. with $4\times10^8$ SRBC. The number of AFC was estimated four days later. The mice were injected s.c. with the mixture of the three drugs (5HTP, HAL, and PHE) at the following dosages: 30, 12 and 12 mg per kg. body weight respectively, two hours before antigen injection and once daily for three successive days.

The hormones were injected s.c. twice a day, in the morning one hour after administration of the drugs and in the evening. The total daily dose of hormones was: GH, 200 µg; TSH, 100 µg and LH, 200 µg.

The results are indicated on the following table VII.

TABLE VII

| Drug Treatment | Nucleated spleen cells ($\times 10^6$) | AFC/$10^6$ spleen cells |
|---|---|---|
| GH + Drugs + SRBC | 95 ± 9 | 14 ± 7 |
| LH + Drugs + SRBC | 125 ± 28 | 35 ± 18 |
| TSH + Drugs + SRBC | 93 ± 16 | 37 ± 27 |
| GH + LH + TSH + Drugs + SRBC | 117 ± 59 | 50 ± 17 |
| Drugs + SRBC | 98 ± 39 | 15 ± 10 |
| SRBC | 203 ± 35 | 282 ± 80 |

The results shown on this table thus show that GH, TSH and LH given singly or in combination did not prevent the drug-induced inhibition of antibody production.

EXAMPLE IX

Protection from and prevention of drug-induced blockage of the immune response to SRBC by a combination of luteotropic hormone (LH), follicle stimulating horone (FSH), and adrenocorticotropic hormone (ACTH).

Groups of five, eight month-old female C3H/He $\times$C57BL/6 F1 hybrid mice were injected i.p. with $4\times10^8$ SRBC. The number of AFC was estimated four days later. The mixture of the three drugs was injected s.c. once a day for four days as a saline suspension at the dose indicated in example I (group C). The hormones alone or in combination were injected s.c. half an hour before the drugs. The total quantity of hormones injected daily was: LH, 200 µg; FSH, 200 µg, ACTH, 5 µg.

The results are apparent from table VIII.

TABLE VIII

| Drug treatment | Nucleated spleen cells ($\times 10^6$) | AFC/$10^6$ spleen cells |
|---|---|---|
| ACTH + Drugs + SRBC | 120 ± 27 | 30 ± 29 |
| FSH + Drugs + SRBC | 133 ± 46 | 47 ± 19 |
| ACTH + LH + Drugs + SRBC | 99 ± 10 | 35 ± 23 |
| ACTH + FSH + Drugs + SRBC | 119 ± 10 | 50 ± 39 |
| ACTH + FSH + LH + Drugs + SRBC | 123 ± 27 | 174 ± 69 |
| SRBC + Drugs | 104 + 26 | 10 ± 4 |
| SRBC | 178 ± 29 | 424 ± 102 |

This example thus shows that most significant protection from the action of the drugs is obtained only when the mice were injected daily with a combination of ACTH, LH and FSH.

The series of experiments of EXAMPLES VIII and IX thus contribute to the clarification of the mechanism of action of the drugs in abolishing specifically the immune response. The comparative results of these two last tables show that the most significant protection is achieved by a combination of LH, FSH and ACTH; that therefore these three hormones in combination seem to be needed for counteracting the effects of the drugs and that consequently the drug composition according to the invention, exerts control on such hormones.

EXAMPLE X

An identical blockade of antibody production was obtained in monkeys. (*Macaca fascicularis*) which were injected intraperitoneally with $4\times10^9$ SRBC and, starting from one to two hours before the SRBC injections, injected sub-cutaneously once a day, during four days with a composition containing 5 HTP, PHE and HAL at doses of 40, 12 and 12 mg/kg of body weight respectively.

Both the primary and secondary immune responses were abolished. The composition did not induce more than a slight sleepiness in the monkeys, such slight sleepiness thus representing an indeed negligible side effect.

The essential role of serotoninergic, dopaminergic and adrenergic systems in controlling or modulating transplantation immune reactions (allogenic skin grafts) was further brought to evidence upon comparing the results obtained with the preferred combination of drugs considered in the foregoing examples and with other drugs mixtures tested by the same model, aiming at a further prolongation of the rejection time and possible elimination of the residual immune reactivity as expressed by late rejection of skin grafts.

EXAMPLE XI

The following "materials and methods" were used.
Animals: Adult, six to twelve week-old outbred male or female Swiss albino and inbred BALB/c mice were used as recipients of skin grafts. The donors were male or female, four to eight week-old inbred C57BL/6 or C3H/He or C57BL/6×CBA/J F1 hybrid mice.

Grafting technique. The conventional technique was used. Round sections of shaved dorsal or ventral skin from donor mice were applied aseptically on the shaved back of recipients. The skin section was sutured with six or eight silk stitches. Sterile, vaseline-impregnated gauze was applied, covered with dry gauze, and an elastic corset was finally adapted. The corsets were removed after 8 to 10 days and the grafts were examined daily. The grafts were considered as viable only until the appearance of the first visible signs of rejection (peripheral infiltration, oedema, induration). Drugs. The following drugs were tested, singly or in combination, for their capacity to retard the rejection of allogeneic skin grafts: (a) brain metabolites: L-5-hydroxytryptophan (5-HTP) and dopamine (DA), (b) Cell membrane receptors' antagonists or agonists: phentolamine (PHE), propanolol (PRO), cyproheptadine (CYP) isoproterenol (IPT). (c) Inhibitors of neurotransmitters synthesis and psychodrugs: haloperidol (HAL), parachlorophenylalanine (PCPA), Valium ® (VA), Librium ® (LI), Laroxyl ® (LA), Taractan ® (TA).

The drugs chosen belong to distinct categories,. It is recalled that their pharmacological actions are: 5-HTP, the precursor of 5-HT, increases 5-HT synthesis; DA is a neurotransmitter and the precursor of catecholamines; PHE, a α-adrenergic antagonist; PRO, a β-adrenergic antagonist; IPT a β- adrenergic agonist; CYP, a serotoninergic antagonist; HAL is a neuroleptic drug which enhances DA turnover by blocking dopaminergic receptors; PCPA inhibits serotonin synthesis; VA,LI are minor tranquillizers; A is a neuroleptic drug and TA and antidepressant.

The doses and schedule of injection of the various drug mixtures

The dosages of each of the components in each of the mixtures tested were as follows: brain metabolites (5HTP, DA), 40 mg; receptors antagonists (PHE, PRO, CYP, HAL) 12 mg; receptors agonists (IPT), 40 mg; inhibitors of neurotransmitters synthesis (PCPA) 150 mg in one single i.p. injection 12 hours before grafting, and psychodrugs (VA, LI, TA, LA), 50 mg per Kg of body weight. These doses are defined for each combination as "dose 1".

The respective dosages are respectively doubled in the "doses 2", and reduced to the halves in the "doses 0.5" hereafter.

About twelve hours before grafting, the albino or BALB/c mice were injected s.c. with the dose 1 of the combination of drugs. A dose 2 was injected one to two hours before grafting. A dose 0.5 was injected one day later and then a dose 0.5 or 1 for the following 5 to 7 days.

The results obtained, that is the effects of the different tested combinations of drugs on the capacity of mice to reject first and second-set allogenic skin grafts, are reported in the following table IX.

TABLE IX

| Combination of drugs | No of mice grafted | First-set graft rejection (days) | Second-set graft rejection after six months (days) |
|---|---|---|---|
| 5HTP, HAL, PHE | 30 | 20-26 | 15-20 |
| 5HTP, HAL, PRO | 20 | 10-13 | — |
| 5HTP, IPT, HAL | 6 | 25-30 | 10-14 |
| 5HTP, HAL, PHE, PRO- | 20 | 12-17 | — |
| DA, HAL, PHE | 20 | 16-20 | — |
| DA, CYP, PHE | 6 | 10-12 | — |
| DA, CYP, PRO | 6 | 8-10 | — |
| DA, PCPA, PHE | 6 | 8-12 | — |
| DA, PCPA, PRO | 6 | 8-10 | — |
| DA, PCPA, HAL, PHE | 7 | 14-16 | — |
| DA, 5HTP, HAL, PHE (C20) | 30 | 30-35 | 26-30 |

The results listed on table IX suggest that a stimulation of serotoninergic and β-adrenergic receptors and a block of dopaminergic and α-adrenergic receptors is needed. This leads to an overall increase of serotonin and to a stimulation, by the increased catecholamines, of the free β-adrenergic receptors. In fact, one can observe that all the combinations of drugs containing the β-adrenergic receptors anatagonist PRO, the serotoninergic blocker CYP, the inhibitor of serotonin synthesis PCPA or DA, but not the dopaminergic antagonist HAL, are ineffective in retarding or even slightly delaying rejection of allogeneic skin grafts. The combination of drugs containing 5HTP, DA, HAL and PHE (defined as C 20) is quite effective in specifically and durably prolonging the allograft rejection time. A possible explanation of this remarkable effect of C 20 is that a proper modulation of the adrenergic system must be combined with a blockade of dopaminergic receptors. DA is the precursor of nerepinephrine and epinephrine. By blocking DA receptors with HAL, the DA turnover and therefore its conversion to catecholamines is stimulated. The addition of DA to a combination of drugs containing HAL results, probably, in enhancement of this conversion. Furthermore, the stimulation of β-adrenergic receptors is increased by the presence of the α-adrenergic blocker PHE.

The substitution of HAL with VA or LI also allowed to achieve a substantial retardation of graft rejection time but it affected only the first-set graft. It seems however clear that, in contrast with the effect of C 20, these other combinations exerted only a temporary immunosuppressive effect.

It has been also found that the composition of the invention should be free of histamine antagonists, as this has been shown by tests performed with the composition C 20 of the invention, which further contained any one of the following histamine antagonists: antazoline, phenindamine and cimetidine (under doses of 5,5 and 20 mg/kg body weight respectively).

It is possible that these blockers of histamine receptors antagonize some components of the combination of drugs C 20.

EXAMPLE XII

This example, —as well as example XIII hereafter— shows a further development of the invention. As a matter of fact the combination of drugs according to the invention not only permits a selective blockade of the immune reaction of a host against selected antigens; but also authorizes a control of the natural immunological barriers of the host's environment which is formed by all the complex regulatory systems which involve antigen—specific lymphocytes, natural killer cells and non-lymphoyd cell populations. This is particularly of advantage in the case of an allogeneic and even xenogeneic bone marrow transplantation and for the "accustoming" or "homing" and proliferation of that allogeneic (or xenogeneic) bone-marrow in the host. These findings which will be illustrated by the results of the tests described hereafter, enabled an allogeneic (or xenogeneic) bone-marrow of a donor to be substituted in the host by engraftment procedures for the endogenous bone marrow, after a destruction thereof, such as by a lethal irradiation, thereby providing the host "chimeric" immunocompetent cells which do not induce a graft-versus-host-disease (GVHD) and which further allow, whenever desired, further organs or tissue of the donor to be transplanted into and to be accepted immunologically by the host. An advantageous method for the substitution of bone-marrow from donor into a recipient host comprises (a) administering, according to the above defined sequence, an effective dose of the drug composition according to the invention and thereafter an effective amount of the donor's bone-marrow in order to achieve a complete blockade of differentiation in the organism of the recipient of all possible antigen-reactive lymphocytes;

(b) destroying the recipient's immune defenses, such as by lethal irradiation, for instance total body irradiation (TBI)

(c) transferring into the immunodeficient recipient the cells of the donor's bone marrow, whereby the number of the cells in the inoculum must be sufficiently high to enable a real seeding and proliferation of these cells in the foreign environment to occur and (d) maintaining the presence of the drug combination according to the invention in the recipient's blood throughout the time necessary for carrying out the mentioned operations, both before (pre-conditioning) and after (post-conditioning) the destruction of the host's endogeneous immune system.

TBI could of course be replaced by other means such as cytotoxic drugs known to destroy the immune system of a host. TBI is however preferred in that it does not involve introducing compounds in the host which might interfere with the components of the drug according to the invention.

It appears that the maintainance of a sufficient concentration of drugs during the first few days following the destruction of the host's endogeneous immune system will prevent the newly arising allogeneic cells from the inoculum to start an immune reaction against the host.

It might be advisable to proceed to a third inoculation of allogeneic (or xenogeneic) bone marrow cells one-two days after irradiation, when the drugs are still circulating (the treatment is prolonged as long as 4–6 days after TBI), in order to compensate for the resistance of the environment and also, to some extent for a certain depleting action which might be caused by the drugs themselves with respect to the younger cells, (particularly stem cells and germinating cells) of the grafted inoculum. In a third and final "adaptation" phase, cells originating from mitosis of the "blocked" allogeneic bone marrow cells inoculated after irradiation in the presence of the drugs start to achieve a complete reconstitution of the immune capacity of the host.

It can be advisable to proceed to further alternate treatment with allogeneic bone marrow cells and drugs later after TBI (15–20 days) in order to supply more allogeneic bone marrow while eliminating possible residual antigen-reactive cells contained in the new inoculum or present in the "chimeric" recipient. The drugs then seek to prevent possible GVHD because of the new antigen-reactive cells in the new inoculum starting an immune reaction against the host even if the host is carrier (chimera) and survives thanks to the successful engraftment of the allogeneic bone marrow in the post-conditioning stage.

The preceding discussion will hereafter be illustrated in a non limitative manner, by the following experimental models:

Transplantation of xenogeneic (rat) bone marrow in lethally irradiated C57BL/6×A/J F1 hybrid mice (a) Animals The recipients of bone marrow were composed of 10–12 weeks old F1 hybrid C57BL/6×A/J female mice. The donors of bone marrow were male or female inbred CARA rats. The choice of the donors was dictated, among others, by the fact that the "take" in such mice of a graft of bone marrow of such rats is known to meet the most severe obstacles. Consequently, the aforementioned rats-mice combination, while it offers some practical advantages (disposition of large quantities of bone marrow), is also established as a difficult one. In fact, C57BL/6 mice and their F1 hybrids offer strong natural resistance to "take" and engraftment of allogeneic and/or xenogeneic bone marrow.

(b) Dose of irradiation

As already determined in many pilot experiments, a dose of 900 rads total body irradiation (TBI) was given. Non-protected C57BL/6×A/J F1 hybrid mice died within 8–12 days. The irradiation apparatus was a Cobalt Gammatron3(6000 Curie). Field size for 900 rads was 30×30 cm. main focus distance 90 cm. The superficial dose from both sides was 652 rads, the central dose was 900 rads. No filters were used.

(c) Dosage of the drugs.

The drugs were administered suspended in saline s.c., in amounts of 0.1–0.2 ml. The total cumulative dosages used were multiples (indicated in the table hereafter by the numbers which follow each time the word "dose") of a "dose 1" which is defined as follows: 40 mg of 5-HTP; 12 mg of PHE and 12 mg of HAL per kg body weight.

(d) Dose of allogeneic or xenogeneic bone marrow cells in the preconditioning phase.

The number of cells in the bone marrow inoculum was between 30 and 100×10$^6$ cells, given intraperitoneally, 6 to 2 hours before lethal irradiation.

(e) Dose of allogeneic or xenogeneic bone marrow cells after TBI (post-conditioning phase).

The second inoculum of bone marrow contained between 20 and 50×10$^6$ cells, and was given intravenously one–two hours post-TBI. Some groups received a third inoculum i.v. (50×10$^6$ cells) 24 or 48 hours post-TBI (group N or O respectively in the table thereafter). This third inoculum contained between 30 and 50×10$^6$ xenogeneic bone marrow cells.

(f) Timing and prolongation of drug treatment before and after TBI

The drugs were injected a few hours before TBI and then once daily for 4 to 8 successive days. Duration of treatment depended on the strain combination and a number of other factors.

(g) Protection with antibiotics.

For one month after TBI, tetracycline and vitamine was supplied to the drinking water, to prevent infection owing particularly to a number of intestinal bacteria, toxemia, as long as the host's resistance thereto is reduced as a result of temporary insufficient population of bone marrow cells in the host's organism.

The results obtained are indicated in table IX hereafter, in which the different abbreviations used have the following meanings:
Syng. B M: Syngeneic bone marrow
xenog. B M: xenogeneic bone marrow
TBI: Total body irradiation

TABLE IX

| No of Group: mice | Pre-conditioning | 900 rads Post-conditioning TBI | SURVIVAL RATE 1 month | 2 months |
|---|---|---|---|---|
| A 20 | — | — | 0 | 0 |
| B 14 | drugs, dose 3 | — | 0 | 0 |
| C 10 | drugs, dose 3 | drugs, dose 3 | 0 | 0 |
| D 10 | — | drugs, syng. BM, drugs (total dose 7) | 1 | 1 |
| E 14 | drugs, dose 3 | syng. BM, drugs (total dose 7) | 11 | 11 |
| F 10 | drugs, dose 3 xenog.BM | drugs (total dose 7) | 0 | 0 |
| G 40 | — | drugs dose 3, xenog. BM drugs (total dose 7) | 4 | 2 |
| H 10 | drugs, dose 3 | xenog BM, drugs (total dose 4) | 9 | 9 |
| I 20 | drugs, dose 3 xenog BM | xenog. BM, drugs (total dose 5) | 15 | 14 |
| L 10 | drugs, dose 3 xenog. BM | xenog. BM, drugs, (total dose 6) | 8 | 4 |
| M 50 | drugs, dose 3 xenog. BM | xenog. BM, drugs (total dose 7) | 27 | 20 |
| N 20 | drugs, dose 3 xenog. BM | xenog. BM, drugs (total dose 7) xenog. BM 24h post TBI | 15 | 15 |
| O 20 | drugs, dose 3 xenog.BM | xenog. BM, drugs (total dose 7) xenog. BM 48h post TBI | 14 | 12 |
| P 10 | xenog. BM | xenog, BM | 6 | 5 |
| Q 10 | drugs C 20 (dose 3) | xenog. BM, drugs (total dose 6) | 2 | 1 |

The table shows the quite impressive survival rates, as evidenced for instance by the results obtained in groups H and N, which the invention provides, upon properly combining the dosages and sequences of administration of the bone marrow cells and the drugs. The results further show that the total dosages of drugs should be adjusted relative to the total amounts of grafted bone marrow because of the sensitivity to drugs of the stem—and germinating cells contained in such bone marrow. Higher amounts of bone marrow should be administered to the host in the instances where higher dosages of drugs would be required to keep under control the possible immune reactions in the host. For instance higher survival rates were obtained in groups N and O which were injected with more bone marrow than in groups L and Q, which received less bone marrow though almost as much drugs in the post conditioning stage.

It is finally significant that the rates of survival which are obtained by resorting to the drug combination of the invention, are roughly the same whether the bone marrow grafted after TBI is of syngeneic or allogeneic origin.

It is of further significance that the peripheral blood granulocytes of the surviving mice of groups H to Q gave constantly positive response in the alkaline phosphatase test, thereby showing that they were of rat origin, and that these mice were shown to indefinitely accept grafts from CARA rats, while being capable of rejecting a third-partner skin graft within 12–14 days. This last result denoted complete reconstitution of the cell-mediated immune capacity in the "chimeric" surviving mice.

EXAMPLE XIII

Grafting of allogeneic bone marrow in AKR mice

Two strains of mice which develop spontaneous solid leukemia (thymoma, lymphosarcoma) were used: the AKR/Cu and the AKR/J were treated as follows:
Pre-conditioning: inoculation with a total dose of "dose 3" of the combination of drugs and injection i.p. of allogeneic bone marrow from leukemia-resistant C57BL/6 donor mice (over $10 \times 10^6$ cells).
Post conditioning: inoculation of allogeneic bone marrow ($50 \times 10^6$ cells i.v.) from the same donor strain (C57BL/6). Continuation of the drug treatment for 4–6 days after TBI (total: dose 4).
Adaptation: a period lasting 3–4 months.

This example thus provides a model for the substitution of bone marrow from leukemia resistant host for the bone marrow of a leukemia-afflicted host.

Biological tests which have been described show that complete tolerance to antigens, at least as far as T-dependent antigens are concerned, can be established by inducing changes in the hormonal response which follow the inoculation of antigens into mice. It must be pointed out that the four drugs given either singly or in pairs gave no or a moderate suppression of immune reactions, but no complete blockade.

The findings which have been described thus reveal a radically different therapeutic and experimental basis for the manipulation and the control of acquired immunity. Its practical application in organ and bone marrow transplantation, in autoimmune disease and in the immunotherapy of some forms of cancer, particularly leukemia and breast cancer, are but a few of the most compelling areas of its application. It would moreover allow a new kind of intervention in the case of hormone-dependent or sensitive-tumors.

The drugs according to the invention can be administered parenterally, rectally or orally. The invention thus relates also to the compositions in which the above combination of compounds is associated with classical pharmaceutical vehicles suitable for the above said administrations. Particularly, the invention concerns injectable suspensions or solutions of the association of the compounds in the dissolved or undissolved state within a sterile physiologically acceptable solution. It also relates to solutions of such drugs which can be administered by perfusion and to compositions for oral administration wherein the mixture of the compounds according to the invention is associated with liquid or solid carriers suitable for oral administration. These examples are of course, in no way of a limiting nature as concerns the different pharmaceutical forms which can be produced and which would contain the associated active principles according to the invention.

The invention further concerns the pharmaceutical compositions containing each of the above defined components, under proportions enabling them to effectively and respectively block the alpha-adrenergic receptors of the cells for catecholamines, block the dopaminergic receptors of the cells increase the synthesis of serotonin and, if need be, inducing a strong reduction, possibly even blockade of growth hormone production in the host's organism in association with a pharmaceutical vehicle.

By way of example and when the components are the preferred ones used in most of the examples, the said compositions may comprise from 5 to 150, particularly from 20 to 150 parts of L-5 hydroxytryptophan;

from 0,25 to 15, particularly from 5 to 15 parts of phentolamine;

from 0,25 to 15, particularly from 5 to 15 parts of haloperidol and:

if need be, from 0,5 to 50, particularly 10 to 50 parts of dopamine (parts in weight).

By way of example, which has no limiting character, one may indicate that when injected sub-cutaneously, the association according to the invention may be administered under daily doses ranging from about 5 to 150 mg/kg, particularly from 20 to 150 mg/kg of L-5-hydroxytryptophan;

about 0,25 to 15 mg/kg, particularly 5 to 15 mg/kg of phentolamine about 0,25 to 15 mg/kg, particularly 5 to 15 mg/kg of haloperidol about 0,5 to 50 mg/kg, particularly 10 to 50 mg/kg of dopamine.

The doses may be further reduced when the drugs are to be administered by perfusion, whereby the constant presence of all of the drug components in the host's blood is easily controllable.

The duration of treatment with compositions according to the invention should be adjusted according to the type and character of the disease as long as may be necessary for obtaining either alleviation or relief of the disease or the sufficient and effective blocking of the immune response sought to be prevented, in the case of graft or transplantation of the antigen tissue or of any appropriate material.

The first administration of the drugs combination ought to be effected before the voluntary graft or administration of the antigenic material or tissue, particularly at the time suitable for blocking the increased production of the gonadotropins which would otherwise, in the absence of the drugs combination, have taken place shortly after said graft or transplantation.

The invention further concerns the laboratory reagents comprising said drug-combination and useful as standards for the comparative assessment of the capability of other compositions under study of effectively blocking the immune response in a host to determined antigens, or more generally for enabling studies in vivo of the behaviour of the organism of a warm-blooded host subjected to determined conditions or brought in the presence of particular agents, while its immune responses to specific antigens or groups of antigens are being controlled by said laboratory reagents. By way of example the drug-combinations of the invention enables the study in "chimeric" AKR mice as described in the last example which of the endogenous bone marrow or of the other environmental, for instance hormonal status, of the AKR—leukemia—susceptible mice can be held as an important parameter with respect to the development of the disease.

We claim:

1. A drug composition effective to selectively control the immune reactions evoked in a host by the administration of selected antigens, which comprises, in combination;

phentolamine, or a pharmacologically acceptable salt thereof, in an amount of about 0.25 to about 15 parts by weight, said amount being effective to block the alpha-adrenergic receptors of the cells of said host for catecholamines;

haloperidol, or a pharmacologically acceptable salt thereof, in an amount of about 0.25 to about 15 parts by weight, said amount being effective to block the dopaminergic receptors of the cells of said host;

a compound selected from the group consisting of serotonin, a precursor thereof, and a pharmacologically acceptable salt thereof, in an amount of about 5 to about 150 parts by weight, said amount being effective to increase the level of serotonin in said host and optionally, as a fourth component, dopamine, or a pharmacologically acceptable salt thereof, in an amount of about 0.5 to 50 parts by weight, said amount being effective to decrease the release of growth hormone in said host.

2. The composition of claim 1 which comprises phentolamine, haloperidol, and the serotonin precursor [L-5-hydroxy-tryptophan]L-5-hydroxytryptophan.

3. The composition of claim 1 which comprises from about 5 to about 15 parts by weight of phentolamine; from about 5 to about 15 parts by weight of haloperidol; and from about 20 to about 150 parts by weight of L-5-hydroxytryptophan.

4. The composition of claim 1, which includes, the compound dopamine in an amount capable of decreasing or blocking the release in said host of the growth hormone.

5. The composition of claim 1 which comprises from about 0.25 to about 15 parts by weight of phentolamine, from about 0.25 to about 15 parts by weight of haloperidol, from about 5 to about 150 parts by weight of the serotonin precursor L-5-hydroxytryptophan and from about 0.5 to about 50 parts by weight of dopamine.

6. The composition of claim 1 which comprises, from about 5 to about 15 parts by weight of phentolamine, from about 5 to about 15 parts by weight of haloperidol, from about 20 to about 150 parts weight of the serotonin precursor, L-5-hydroxytryptophan and from about 10 to about 50 parts of dopamine.

7. A pharmaceutical composition comprising a combination drug composition as defined in any one of claims 1, 2, 3, 4, 5, or 6 in association with a pharmaceutically acceptable vehicle.

8. The pharmaceutical composition of claims 1, or 2 in the form of an injectable suspension.

9. The pharmaceutical composition of claims 1, or 2 in the form of a solutin suitable for administration by perfusion.

* * * * *